(12) United States Patent
Fargahi

(10) Patent No.: US 10,299,949 B2
(45) Date of Patent: May 28, 2019

(54) RELEASE DEVICE FOR RELEASING A MEDICAL IMPLANT FROM A CATHETER, AND CATHETER

(71) Applicant: BIOTRONIK AG, Buelach (CH)

(72) Inventor: Amir Fargahi, Buelach (CH)

(73) Assignee: BIOTRONIK AG, Buelach (CH)

( * ) Notice: Subject to any disclaimer, the term of this patent is extended or adjusted under 35 U.S.C. 154(b) by 328 days.

(21) Appl. No.: 14/610,279

(22) Filed: Jan. 30, 2015

(65) Prior Publication Data
US 2015/0238339 A1    Aug. 27, 2015

Related U.S. Application Data

(60) Provisional application No. 61/944,078, filed on Feb. 25, 2014.

(51) Int. Cl.
| A61F 2/95 | (2013.01) |
| A61F 2/97 | (2013.01) |
| A61F 2/966 | (2013.01) |

(52) U.S. Cl.
CPC ........... *A61F 2/966* (2013.01); *A61F 2/97* (2013.01); *A61F 2002/9517* (2013.01)

(58) Field of Classification Search
CPC ..... A61F 2/97; A61F 2/966; A61F 2002/9517
See application file for complete search history.

(56) References Cited

U.S. PATENT DOCUMENTS

| 8,778,006 | B2 | 7/2014 | Fargahi et al. | |
| 2002/0004676 | A1* | 1/2002 | Wallace | A61B 17/12118 |
| | | | | 623/1.12 |
| 2005/0080476 | A1 | 8/2005 | Gunderson et al. | |
| 2006/0259124 | A1* | 11/2006 | Matsuoka | A61F 2/966 |
| | | | | 623/1.12 |
| 2007/0244540 | A1* | 10/2007 | Pryor | A61F 2/95 |
| | | | | 623/1.11 |
| 2009/0270969 | A1* | 10/2009 | Fargahi | A61F 2/95 |
| | | | | 623/1.11 |
| 2012/0059448 | A1* | 3/2012 | Parker | A61F 2/95 |
| | | | | 623/1.11 |
| 2013/0184805 | A1* | 7/2013 | Sawada | A61F 2/97 |
| | | | | 623/1.11 |

FOREIGN PATENT DOCUMENTS

| EP | 1844739 A1 | 10/2007 |
| EP | 2111826 A1 | 3/2009 |
| WO | 2007022395 A1 | 2/2007 |
| WO | 2010120670 A1 | 10/2010 |
| WO | 2010120671 A1 | 10/2010 |

\* cited by examiner

*Primary Examiner* — Martin T Ton
(74) *Attorney, Agent, or Firm* — Greer, Burns & Crain, Ltd.; Steven P. Fallon

(57) ABSTRACT

A release device for releasing a medical implant from an insertion device, in which the implant can be released by a relative movement between a first and a second insertion element, wherein the insertion device has a proximal end, which faces the user during use, and a distal end, which is distanced from the user during use. Between the proximal and the distal end, a shortening region is provided, in which, when generating a targeted relative movement between the first and the second insertion element of the insertion device, a length of at least one of the insertion elements between the proximal end and the distal end can be shortened.

13 Claims, 5 Drawing Sheets

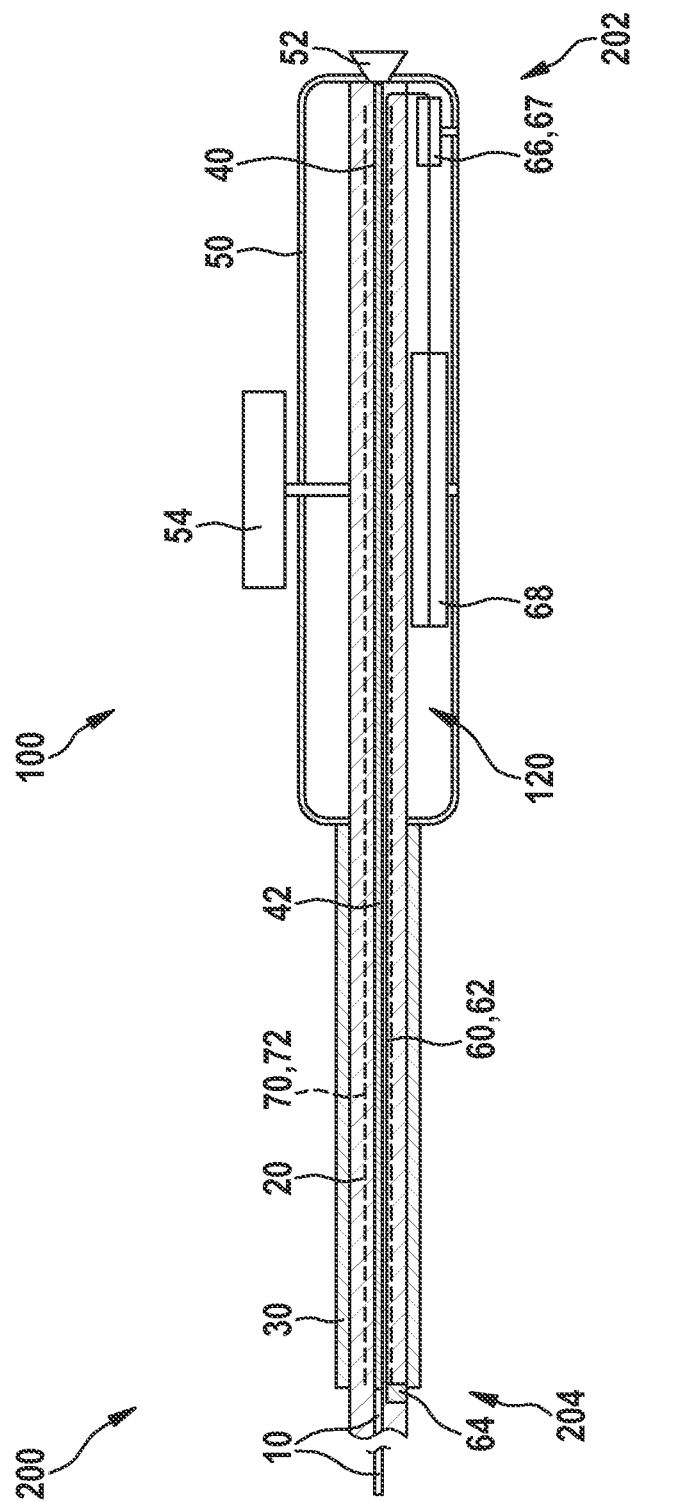

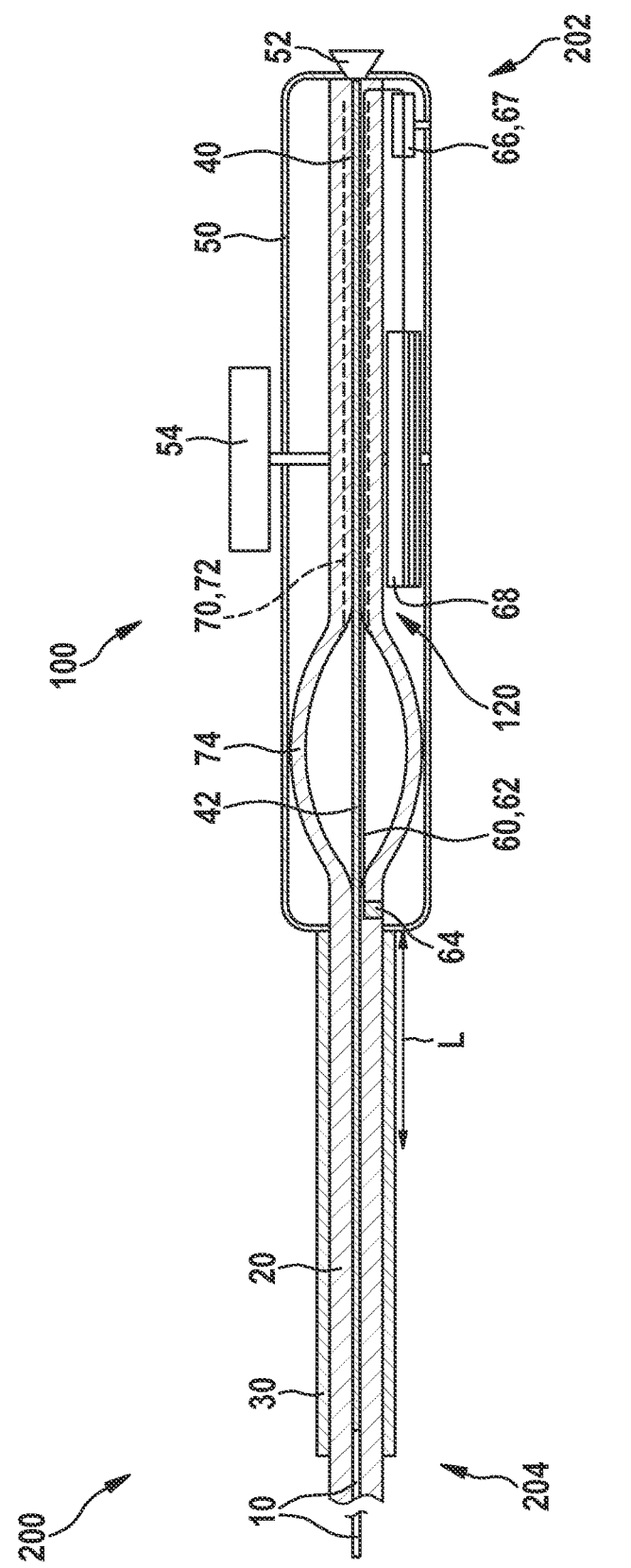

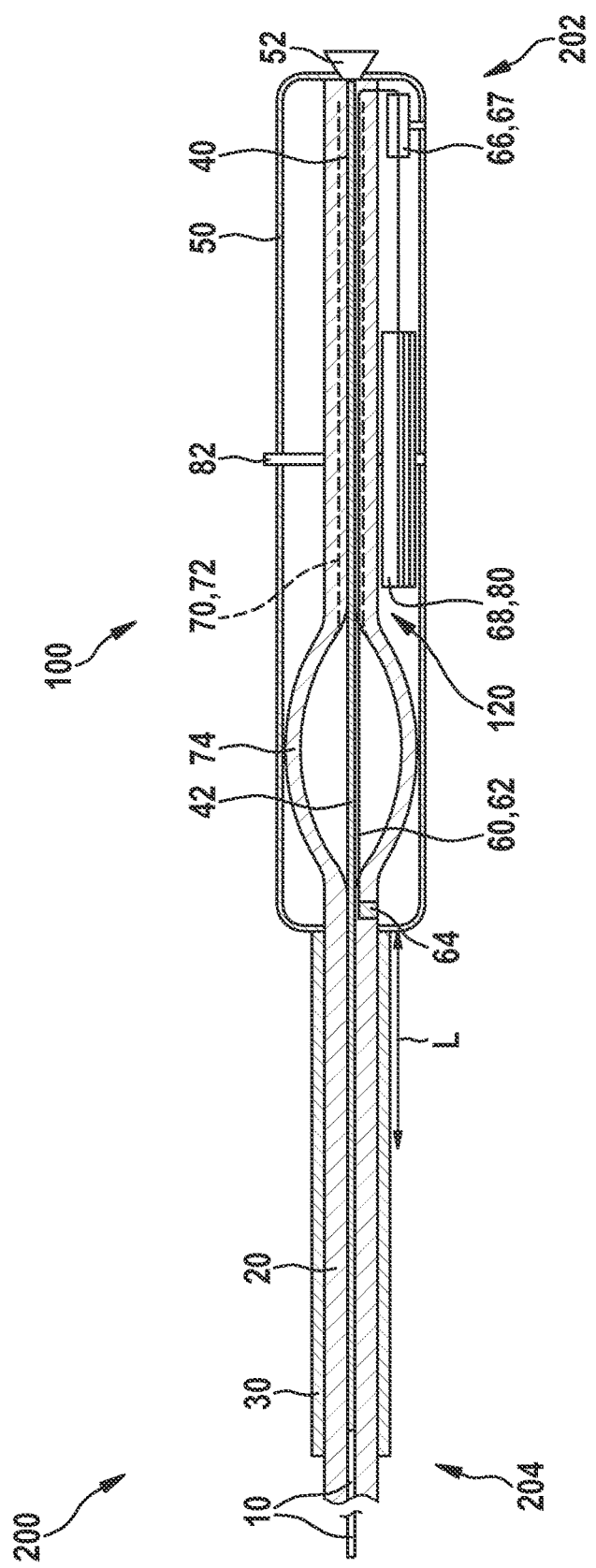

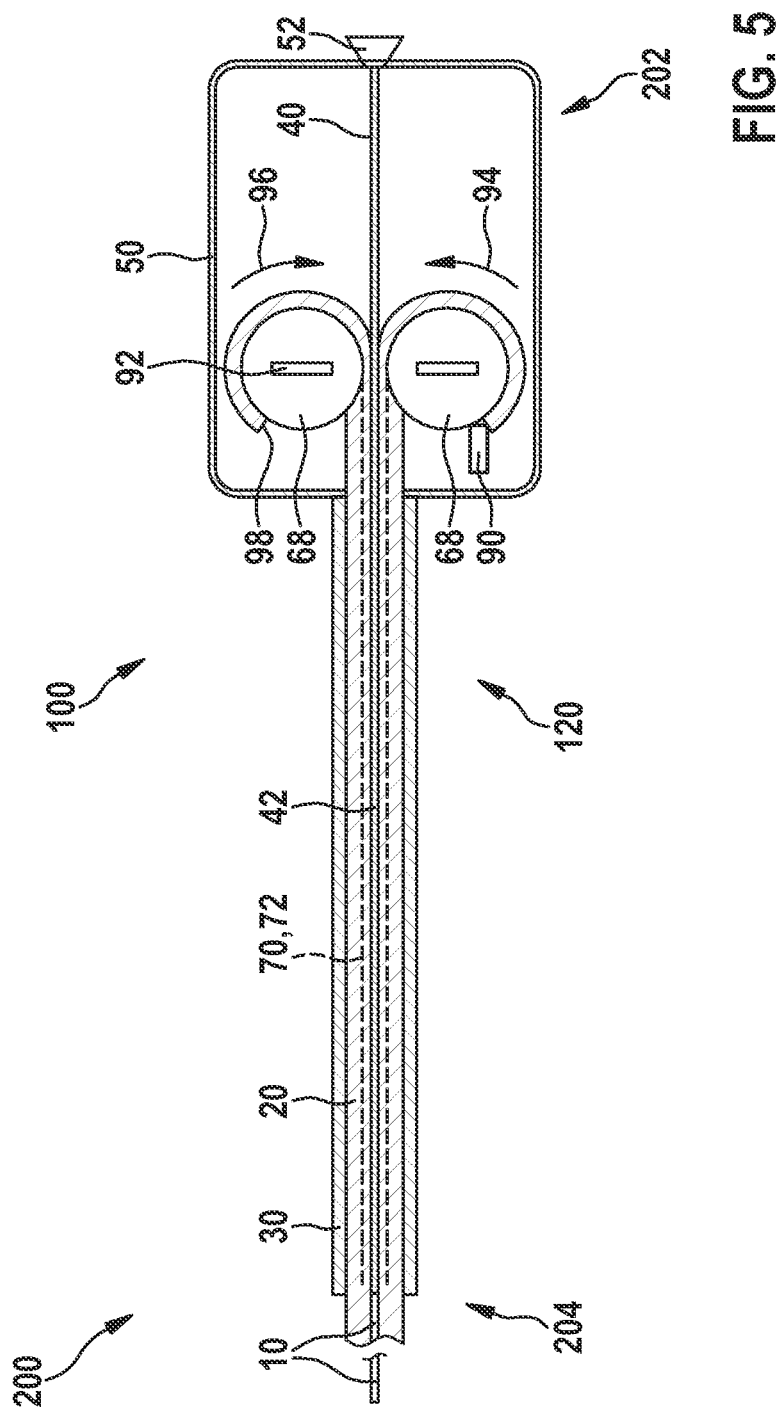

RELEASE DEVICE FOR RELEASING A MEDICAL IMPLANT FROM A CATHETER, AND CATHETER

PRIORITY CLAIM

This application claims priority under 35 U.S.C. § 119 from prior U.S. Provisional Application No. 61/944,078, filed Feb. 25, 2014.

FIELD OF THE INVENTION

A field of the invention is medical implants. The invention relates to a release device for releasing a medical implant from a catheter and to a catheter in the form of a release device.

BACKGROUND

In the field of medicine, implants are often used that are introduced into an animal and/or human body either permanently or at least for a relatively long period of time in order to carry out replacement functions. For example, these implants could include heart pacemakers, brain pacemakers for Parkinson's patients, cardiac implants, cochlear implants, retinal implants, dental implants, implants for joint replacement, vessel prostheses, or stents.

Implants are connected to catheters for insertion into the body and have to be able to be placed precisely at the site for use and released in a controlled manner. An example technique to release the implant is by a sliding motion.

Known catheters are sized according to a dependent relationship between the overall length of the catheter and the length of the implant, for example of a stent. The longer is the stent, the longer is the overall length of the catheter. Thus, the overall length for a catheter for insertion of a stent 200 mm long is at least 180 mm longer than the same catheter with a stent 20 mm long. This impairs the release of the implant at the intended site.

For the doctor, this necessitates use of a longer guide wire, which, when releasing the implant, leads to a longer path of displacement of the catheter over the guide wire and to complicated handling. From an ergonomic point of view the handling of such a long system is awkward for the user. The user requires both hands to release the implant using a release device known as the "pull-back system" provided for this purpose.

A release system for a long stent is known from EP 1 844 739 A1 and has a short handle. In order to release the stent in the site for use, an outer shaft is retracted, wherein it is led away by a branch from the handle.

SUMMARY OF THE INVENTION

A preferred embodiment provides a release device for releasing a medical implant from an insertion device. The release device releases the implant by a relative movement between a first and a second insertion element. The insertion device has a proximal end, which faces a user during use, and a distal end, which is distanced from the user during use. Between the proximal and the distal end, a shortening region is provided, in which, when generating a targeted relative movement between the first and the second insertion element of the insertion device, a length of at least one of the insertion elements between the proximal and the distal end can be shortened.

BRIEF DESCRIPTION OF THE DRAWINGS

The invention is explained in greater detail hereinafter by way of example on the basis of exemplary embodiments illustrated in drawings, in which:

FIG. 2 schematically shows a further embodiment of an insertion having a slitted region of an outer shaft in the proximal region within a handle of the insertion device and with a stabilizing shaft connected thereto;

FIG. 3 schematically shows the embodiment according to FIG. 2 with partly retracted outer shaft;

FIG. 4 schematically shows an embodiment similar to FIG. 1 with partly refracted outer shaft and electric motor as a drive of a winding mechanism; and FIG. 5 schematically shows a further embodiment of an insertion device having a slitted region of an outer shaft in the proximal region within a handle of the insertion device with two winding units for winding up the outer shaft.

DETAILED DESCRIPTION OF THE PREFERRED EMBODIMENTS

Figure 1:
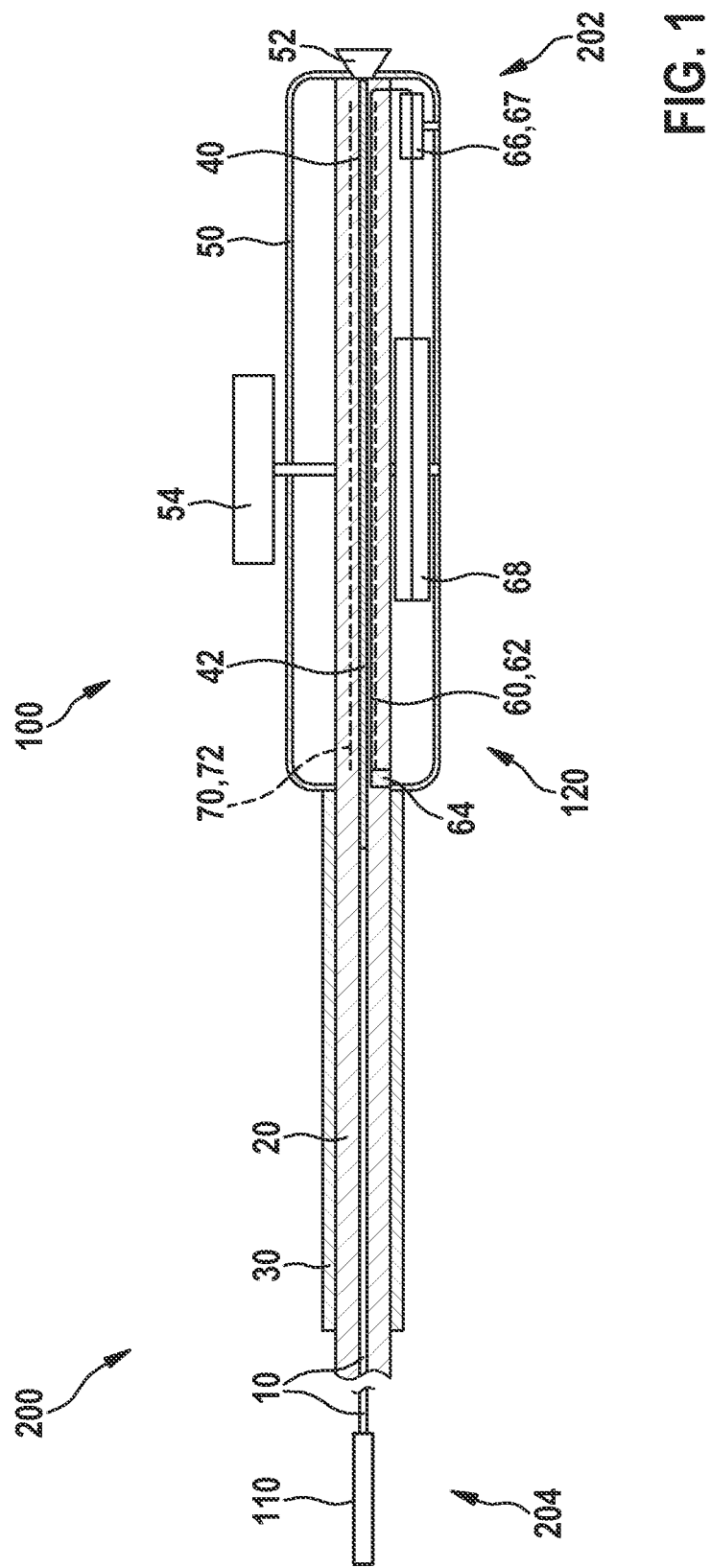
FIG. 1 schematically shows a first embodiment of an insertion device having a slitted region of an outer shaft in the proximal region within a handle of the insertion device.

A preferred embodiment release device for releasing a medical implant from an insertion device releases the implant by a relative movement between a first and a second insertion element. The insertion device has a proximal end, which faces a user during use, and a distal end, which is distanced from the user during use. Between the proximal and the distal end, a shortening region is provided, in which, when generating a targeted relative movement between the first and the second insertion element of the insertion device, a length of at least one of the insertion elements between the proximal and the distal end can be shortened.

Preferred insertion elements are shortened by being folded up and/or by being rolled up. The design of preferred release devices advantageously allows a simple relative displacement of an insertion element, for example of an outer shaft over an inner element, for example an inner shaft. The insertion element, for example outer shaft, can be pre-slitted with axially directed slits and can be folded up in the proximal region and thus shortened. The outer shaft can also be rolled up for example at the proximal end and thus shortened. Advantageously, it is not necessary to extract the outer shaft from the handle, which would require a suitable seal. Further, a length of an insertion device in the form of such a release device is independent of a length of the implant.

Preferred release devices provide comfortable handling, even with long stents. Preferred embodiments of the invention provide a catheter for inserting a long stent.

The release device according to the invention is used, for example, in the release of self-expanding stent systems for retracting a protection of balloon-expanding stents, or for retracting a protection of coated balloons.

In accordance with a preferred embodiment, a winding mechanism can be provided in the shortening region. This mechanism can be accommodated in a compact and space-saving manner at a suitable proximal location, for example in a handle. The insertion element, which is displaced in order to release the implant, in particular is retracted from the distal end toward the proximal end, remains within the release device.

In accordance with a preferred embodiment, a traction mechanism can be provided which acts on at least one of the insertion elements in order to implement the relative movement between the first and the second insertion element. In particular, the traction mechanism may have a traction thread, which can be wound up using the winding mechanism, wherein at least one of the insertion elements can be folded once or more to reduce the length thereof. A pre-slitted outer shaft can advantageously be folded up in the proximal region and therefore shortened by drawing the traction thread, which is fastened to the outer shaft, toward the proximal end and winding it up, thus entraining the outer shaft, which in so doing can be folded in the pre-slitted region In accordance with a preferred embodiment the winding mechanism may include a deflection mechanism, which can cooperate with the fraction mechanism. In particular, the deflection mechanism may include at least two deflection rolls. A pulley mechanism may favorably be integrated in the release device. Depending on the number of deflection rolls, the force to be applied here, by means of which the traction mechanism is to be actuated, can be reduced in a manner as is known with pulleys.

In accordance with a preferred embodiment at least one of the insertion elements can be wound up in order to shorten the length thereof. This can be provided alternatively or additionally to the folding of the pre-slitted insertion element. Here, two winding mechanisms can be provided, which each receive one half of the pre-slitted insertion element.

In accordance with a preferred embodiment the winding mechanism can be coupled to a handwheel. This can be operated comfortably by hand.

In accordance with a preferred embodiment the winding mechanism can be coupled to a motor. The motor is advantageously integrated in a handle of the insertion device and can be operated by means of a start-stop button on the handle. Alternatively, a winding mechanism can be provided, which can be actuated with spring force.

In accordance with a further aspect of the invention an insertion device for insertion of a medical implant is provided, the implant being releasable by a relative movement between a first and a second insertion element, in the form of a release device for releasing the medical implant. Between the proximal and the distal end, a shortening region is provided, in which, when generating a targeted relative movement between the first and the second insertion element of the insertion device, a length of at least one of the insertion elements between the proximal and the distal end can be shortened, wherein the shortening region is arranged in a handle at the proximal end.

A folding up of the insertion element, for example of the outer shaft, enables the embodiment of a short handle. The overall length of the catheter is thus reduced, which leads to simpler handling and to a reduced path of displacement of the catheter over the guide wire. The user needs to use only one hand in order to release the stent.

In accordance with a preferred embodiment at least one of the insertion elements may include a slitted region. The slitted region may include one or more slitted segments, having at least one axial slit along the axial extent thereof.

In accordance with a preferred embodiment at least one of the insertion elements may include a slitted region having at least two axial slits in the peripheral direction. The slits can be arranged in a diametrically opposed manner for example, or a number of slits can be arranged around the center axis of the insertion element, in particular symmetrically. The number of slits around the center axis and/or in the axial direction may expediently be selected in accordance with one or more parameters, such as material and thickness of the insertion element and also length of the implant. For example, an insertion element in which two or more slitted segments follow one another in the axial direction is more stable than one insertion element having just one longer slitted segment.

In accordance with a preferred embodiment the slitted region can be arranged within the handle. The insertion element, for example the outer shaft, is retracted in the unslitted region, and the risk of a torn outer shaft is reduced.

In accordance with a preferred embodiment the slitted region may extend into a shaft bordering the handle. The insertion element, for example the outer shaft, is retracted in the unslitted region, and the risk of a torn outer shaft is reduced.

In the figures, functionally like or similarly acting elements are denoted in each case by like reference signs. The figures include schematic illustrations, which will be understood by artisans FIG. 1, shows a first embodiment of an insertion device 200 according to one aspect of the invention in the form of a catheter in the form of a release device 100 according to another aspect of the invention. The release device 100 serves to release a medical implant 110 from an insertion device 200, in which the implant 110 can be released by a relative movement between a first insertion element 10, for example an inner shaft 10, and a second insertion element 20, for example an outer shaft 20. During the insertion, the implant 110 is arranged on the inner shaft 10 and is covered by the outer shaft 20. A guide wire (not illustrated) can be guided through the inner shaft 10. The implant 110 is normally released by retracting the outer shaft 20 with respect to the inner shaft 10, and the implant 110 is released and deposited at the desired location.

The insertion device 200 has a proximal end 202, which faces a user during use, and a distal end 204, which is distanced from the user during use. The implant 110 is indicated schematically at the distal end 204 of the insertion device 200. Between the proximal end 202 and the distal end 204, a shortening region 120 is provided, in which, when generating a targeted relative movement between the outer shaft 10 and the inner shaft 20 of the insertion device 200, a length of at least one of the insertion elements 20, for example of the outer shaft 20, between the proximal end 202 and the distal end 204 can be shortened.

At the proximal end 202, a handle 50 is arranged, in the interior of which the release device 100 is located. A winding mechanism 68 can be actuated from outside using a handwheel 54. In this exemplary embodiment a traction mechanism 60 in the form of a traction thread 62 is provided, which is fastened to the outer shaft 20 and is guided via a deflection mechanism 66, for example a deflection roll 67, to the winding mechanism 68 in the handle 50. The handle 50 can be provided with a conventional valve 52, for example a Luer taper, by means of which air can be removed simultaneously from the guide wire lumen in the inner shaft 10 and from the region between the outer shaft 10 and the inner shaft 10.

The outer shaft 20 includes a slitted region with a segment 70 that is pre-slitted in the axial direction, wherein the traction thread 62 is fastened to the distal end of the pre-slitted segment 70 using a fastening 64. The number of pre-slitted segments 70 is to be selected depending on the dimension and material of the outer shaft 20. Slits 72 are expediently formed in pairs in a diametrically opposed manner in the one or more pre-slitted segment(s). More slits 72, for example three or more, may also be arranged on the periphery and are distributed symmetrically on the periphery. In the slitted region, the inner shaft 10 is surrounded by a stabilizing shaft 40, for example a metal shaft 42.

The inner shaft 10 is surrounded by the outer shaft 20. In the vicinity of the handle 50, the outer shaft 20 is surrounded by a stabilizing shaft 30. The slitted region of the outer shaft 20 may also be arranged partly in the stabilizing shaft 30 of the catheter. The stabilizing shaft 30 prevents an undesirable folding of the outer shaft 20 beyond the handle 50.

FIG. 2, to explain the invention, shows a further embodiment of an insertion device 200 according to one aspect of the invention in the form of a catheter in the form of a release device 100 according to another aspect of the invention. The mechanism corresponds largely to that in FIG. 1, with reference being made to the description thereof in order to avoid unnecessary repetitions.

By contrast with FIG. 1, the slitted region of the outer shaft 20 now also extends in the stabilizing shaft 30, such that, when retracting the outer shaft 20 into the handle 50, a greater length is available.

FIG. 3 shows the mechanism from FIG. 2 with partly retracted outer shaft 20, wherein the implant (not illustrated) is already partly released. The outer shaft 20 is retracted by a length L. The outer shaft 20 thus opens in the slitted region, forms bulges 74 on both sides and folds up when refracted further.

FIG. 4 shows a variant corresponding to the embodiments in FIG. 1 and FIG. 2, in which the handwheel 54 is replaced by a switch-on button 82 and a motor is used as a winding mechanism 68. This further facilitates the operation of the release device 100. Different winding speeds can also be implemented as a result. Alternatively, a winding mechanism that is rotated with the aid of spring force can also be provided.

Generally, a pulley mechanism can also be integrated in the handwheel 50 with two or more deflection rolls 67 in order to wind up the traction thread 62. Here, as is known, the number of load-bearing cables over which the load can be distributed is decisive for the tractive force that has to be applied by the user. A wide range of mechanisms of pulleys known per se can be used for this purpose.

FIG. 5 shows an alternative embodiment of the invention in which the winding mechanism 68 may include at least two rolls, which are arranged symmetrically on the catheter and which can be rotated synchronously in opposite directions of rotation 94, 96, for example using the grip 92 to turn the rolls. Here, at least two halves of a pre-slitted segment 70 of the outer shaft 20 can be divided into separate surface regions, which can each be grasped and wound up separately by the winding mechanism 68. This facilitates the winding process, which can be implemented with a low application of force.

The winding can be performed for example with the aid of a motor (for example an electric motor).

The halves of the pre-slitted segment 70 can be connected at their ends 98 to the rolls. To lock the rolls, a safety pin 90 can be provided, which can be released if the outer shaft 20 is to be retracted.

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A release device for releasing a medical implant from an insertion device, in which the implant can be released by a relative sliding movement between inner and outer shafts, wherein the outer shaft has a proximal end, wherein the proximal end faces the user during use, and a distal end, which is distanced from the user during use, and wherein between the proximal and the distal end, a shortening region is provided separated from the proximal end and the distal end, in which, when generating a targeted relative movement between the inner and outer shafts of the insertion device, a length of the outer shaft between the proximal end and the distal end can be shortened through the shortening region by outwardly bulging the shortening region and folding upon further shortening the shortening region, wherein the shortening region comprises a pre-slitted region with at least one slitted segment along the axial extent thereof, and further comprising a winder that winds a thread that is fastened to the distal end of the pre-slitted region.

2. The release device as claimed in claim 1, wherein the thread comprises a traction thread that acts on the outer shaft to implement the targeted relative movement between the first and the second insertion element.

3. The release device as claimed in claim 2, wherein the traction thread is controlled by at least one deflection roll.

4. The release device as claimed in claim 3, wherein the at least one deflection roll comprises at least two deflection rolls.

5. The release device as claimed in claim 1, wherein the winder is coupled to a handwheel.

6. The release device as claimed in claim 1, wherein the winder is coupled to a motor.

7. The insertion device as claimed in claim 1, wherein the shortening region comprises a pre-slitted region with at least one slitted segment along the axial extent thereof, wherein at least a portion of the pre-slitted region is contained within the handle.

8. An insertion device for inserting a medical implant, which can be released by a relative sliding movement between inner and outer shafts, the outer shaft being pre-configured to shorten in a shortening region between a proximal end and a distal end of the outer shaft, wherein the shortening region is separated from the proximal and distal ends, wherein the shortening region is configured so that a length of the cuter shaft can be shortened through the shortening region by outwardly bulging the shortening region and folding upon further shortening the shortening region, and wherein the shortening region comprises a pre-slitted region with at least one slitted segment along the axial extent thereof, and further comprising a winder that winds a thread that is fastened to the distal end of the pre-slitted region.

9. The insertion device as claimed in claim 8, wherein the pre-slitted region comprises at least two axial slits in the peripheral direction.

10. The insertion device as claimed in claim 9, wherein the entire pre-slitted region is arranged and contained within the handle.

11. The insertion device as claimed in claim 9, wherein the pre-slitted region extends into a shaft bordering the handle.

12. A release device for releasing a medical implant from an insertion device, in which the implant can be released by a relative movement between inner and outer shafts, the outer shaft being pre-configured to fold in a shortening region thereof, wherein the insertion device has a proximal end contained within a handle, wherein the proximal end faces the user during use, and a distal end, which is distanced from the user during use, and wherein between the proximal and the distal end, the shortening region is provided, in which, when generating a targeted relative movement between the inner and outer shafts of the insertion device, a length of the outer shaft between the proximal end and the distal end can be shortened by folding the shortening region, wherein the shortening region is a region of the outer shaft that is separated from a proximal end of the outer shaft, and wherein the proximal end of the outer shaft abuts an interior portion of the handle, and wherein the shortening region is configured to outwardly bulge and fold upon further shortening during the relative movement between the inner and outer shafts.

13. The device of claim 12, wherein a thread is fastened to the outer shaft at a distal end of the pre-slitted region.

* * * * *